United States Patent [19]

Kawabe et al.

[11] Patent Number: 5,559,255

[45] Date of Patent: Sep. 24, 1996

[54] METHOD OF RECOVERING ETHYLENE OXIDE

[75] Inventors: Kazuki Kawabe; Kazuhiko Murata; Toshiyuki Furuya, all of Yokkaichi, Japan

[73] Assignee: Mitsubishi Chemical Corporation, Tokyo, Japan

[21] Appl. No.: 523,199

[22] Filed: Sep. 5, 1995

[30] Foreign Application Priority Data

Sep. 8, 1994 [JP] Japan .................................... 6-214919

[51] Int. Cl.⁶ ....................... C07D 301/32; C07D 303/04
[52] U.S. Cl. ........................... 549/538; 549/541; 549/542
[58] Field of Search ................................ 549/538, 541, 549/542

[56] References Cited

U.S. PATENT DOCUMENTS

| | | |
|---|---|---|
| 3,948,621 | 4/1976 | Cocuzza et al. . |
| 4,221,727 | 9/1980 | Tsang et al. ................ 549/538 |
| 4,233,221 | 11/1980 | Raines et al. . |
| 4,437,938 | 3/1984 | Bhise et al. . |
| 4,437,939 | 3/1984 | Bhise et al. . |
| 5,145,561 | 9/1992 | Marquis et al. . |

OTHER PUBLICATIONS

J. Falbe et al., *Römpp Chemie Lexikon,* 9th Edition, pp. 2748–2749 (1991).
I. P. Mukhlenov et al., *Chemical Abstracts,* 87(2), Abstract No. 87:10667h (1977).

*Primary Examiner*—Joseph E. Evans
*Attorney, Agent, or Firm*—Wenderoth, Lind, & Ponack

[57] ABSTRACT

The present invention relates to a method of recovering ethylene oxide comprising the steps of:

bringing a mixed gas containing ethylene oxide into contact with an absorbent so as to cause the absorbent to absorb the ethylene oxide; and stripping and separating said ethylene oxide to recover it from the absorbent, where the absorbent contains propylene carbonate. By employing the present invention, it is possible to reduce the heat recovery loss resulting from cooling the absorbent at the time of transfer from the stripping step to the absorption step, to about one-third that compared with a conventional system using water, without producing the by-product ethylene glycol.

13 Claims, 4 Drawing Sheets

METHOD OF RECOVERING ETHYLENE OXIDE

BACKGROUND OF THE INVENTION

FIELD OF THE INVENTION

The present invention relates to a method of recovering ethylene oxide. More specifically, the present invention relates to a method comprising the following steps;

Introducing a reaction product gas containing ethylene oxide, obtained by the vapor phase catalytic oxidation of ethylene with oxygen over a silver catalyst, to an ethylene oxide absorption tower;

absorbing ethylene oxide in an absorbent containing propylene carbonate; and supplying the absorbent to a stripping tower to recover ethylene oxide by stripping and subsequent separation.

DESCRIPTION OF THE RELATED ART

Conventionally, ethylene oxide is recovered according to the following steps using an absorbent containing water as a main component. A reaction product gas containing 0.5 to 5% ethylene oxide, obtained by the vapor phase catalytic oxidation of ethylene with oxygen over a silver catalyst, is introduced to an ethylene oxide absorption tower where it is counter-flow contacted with an absorbent (maintained at a temperature of 5 to 40° C.) having water as a main component, within which the ethylene oxide is absorbed. The absorbent is then sent to an ethylene oxide stripping tower to recover ethylene oxide by withdrawing a gas containing mainly ethylene oxide from the top of the tower at a temperature of 85 to 140° C. by depressurizing and stripping with heating steam. A gas having the recovered ethylene oxide as a main component, and which also contains water, inert gases, such as nitrogen and carbon dioxide, hydrocarbons, such as methane, ethane and ethylene, and aldehydes, undergoes a purification procedure in order to obtain highly purified ethylene oxide as a product. The water remaining after the stripping of ethylene oxide is recycled to the absorption tower for reuse. There are, however, two main drawbacks in this method of recovering ethylene oxide employing an absorbent containing water as a main component.

One problem is the by-production of ethylene glycol occurring at the time of recovery. In the process of the absorption of ethylene oxide gas, transfer of the absorbent, and stripping by heating, it is impossible to prevent the conversion of some amount of ethylene oxide to ethylene glycol, because water itself produces ethylene glycol by reacting with ethylene oxide. This amount reaches 3 to 15% of the whole ethylene oxide. There is a large demand for obtaining a product comprising pure ethylene oxide without the production of ethylene glycol due to recent economic and social circumstances. Thus, in systems using water as an absorbent, there is a large products loss. Even if ethylene glycol is the target product, and is converted from a part or all of ethylene oxide, it is still difficult, to obtain ethylene glycol as a highly purified industrial product, because this type of ethylene glycol, the by-product from an ethylene oxide recovery step, contains a high amount of impurities such as aldehydes and organic acids produced in the oxidation process of ethylene.

The second problem is energy loss at the time of recovery. The absorption of ethylene oxide preferably proceeds at a relatively low temperature such as 5 to 40° C., while the stripping step requires higher temperatures such as 85 to 130° C. Therefore, when employing an absorbent containing water as a main component, a heating operation in the transfer process (from the absorption tower to the stripping tower), and a cooling operation in the recycling process (from the stripping tower to the absorption tower) are repeated. It is difficult to recover energy economically from warm water, though a part of the energy is recovered in those processes by heating other fluid having a low temperature. Generally, it is difficult to recover energy from water in which the temperature thereof is below 70 to 100° C., thus the energy is discharged from the process as heat dissipation to cooling water, resulting in a large loss of heat energy, since water has a high specific heat.

Some methods have been proposed to overcome the problems caused by the use of water as an absorbent for ethylene oxide.

U.S. Pat. No. 3,948,621 discloses a method of separating ethylene oxide and carbonate dioxide simultaneously from a mixed gas obtained from catalytic oxidation of ethylene by oxygen using methanol as an absorbent.

As the specific heat of methanol is less than half of water, the problem of heat loss when water is used can be decreased, if a suitable heat recovery system can be set up. The boiling point of methanol, however, is low at 65° C., and like water, methanol produces methyl glycol ether by reacting with ethylene oxide. Therefore, absorption of ethylene oxide must proceed at a low temperature, such as −15 to −50° C., and so setting up a suitable heat recovery system is very difficult. When the absorption of ethylene oxide proceeds at a higher temperature than mentioned above, the splash loss of methanol increases, and moreover, the gas would contain methanol at the time of recycling to the oxidation reactor after the absorption and removal of ethylene oxide, which produces such undesirable effects as the burning of alcohol, etc., in regard to the oxidation process of ethylene.

U.S. Pat. No. 4,437,938 and U.S. Pat. No. 4,437,939 disclose methods using supercritical or (near) supercritical carbon dioxide and water at the same time as absorbents. Here, the processes, until the absorption of ethylene oxide using water from the gas produced from ethylene by the oxidation reactor, are the same as conventional methods,. The water which absorbed ethylene oxide therein is then placed in contact with (near) supercritical carbon dioxide without heating, and ethylene oxide is extracted to the carbon dioxide solvent. The carbon dioxide is, next, separated from the resulting extraction by distillation under reduced pressure to recover ethylene oxide. It is then compressed to increase pressure by a compressor to be recycled as an extracting solvent. According to this method, it is possible to prevent the heat recovery loss associated with water heating and cooling. This method, however, has two drawbacks. One is that although this method may prevent heat recovery loss, as the required amount of (near) supercritical carbon dioxide is as large as approximately 35 times the amount of ethylene oxide which is supposed to be absorbed therein, and examples of sufficient pressure for the extraction is 88 kg/cm².G and for the separation of ethylene oxide and carbon dioxide is 73 kg/cm².G, with the large pressure difference of 15 kg/cm².G, a huge amount of energy is required to raise the pressure of the carbon dioxide. In other words, the heat recovery loss merely has the tendency to change to a pressure raising energy loss. Furthermore, to maintain this (near) supercritical condition of carbon dioxide (critical condition of carbon dioxide is at 31° C., 75.1 kg/cm².G), the operating pressure has to be increased as mentioned above, resulting in high equipment costs compared with conventional methods operating with a stripping pressure of about 0.1 to 2 kg/cm².G. Consequently, this method does not provide a feasible solution.

U.S. Pat. No. 4,233,221 discloses a method using ethylene carbonate as an absorbent for ethylene oxide. The specific heat of ethylene carbonate is only about 40% that of water, and its ethylene oxide absorbing power is higher than water, its splashing loss is lower than water because its boiling point is high at 239° C. Moreover, ethylene carbonate is stable and does not directly react with ethylene oxide. By using ethylene carbonate the by-production of ethylene glycol can be avoid and heat recovery loss can be reduced approximately 60%.

U.S. Pat. No. 4,233,221, however, has the following drawbacks.

First, it is not possible to achieve the above mentioned decrease in heat recovery loss because the high solidifying point of ethylene carbonate impedes operating with an efficient amount of absorbent. According to conventional methods using water, the temperature of the absorption operation is 5 to 40° C., which is too low to operate with ethylene carbonate whose solidifying point is 39° C. To perform the whole operation without any troubles with solidifying, the process should be practically maintained at least at above 50° C. That means the absorption operations employing ethylene carbonate should be maintained at a temperature over 10° C. higher than operation using water. The absorbing power of this operation correspondingly decreases, so that the amount of circulating absorbent must be increased, greatly impairing the reduction of heat recovery loss between absorption and stripping.

Secondly, the high solidifying point of ethylene carbonate causes some serious problems to arise regarding operation, insulation and maintenance, such as the problem that even when the plant is not operated, it is necessary to keep a large amount of absorbent heated, resulting in higher operating costs for the heating system. Also, there is the tendency for pipe blocking or a decline in heat exchange efficiency due to partial solidifying on the contact surface between the ethylene carbonate and the cooling water since even though the temperature of ethylene carbonate is kept high as mentioned above, a temperature difference of usually 15 to 20° C. between the cooling water and ethylene carbonate is required to indirectly exchange-heat from one to another. As described above, no method provides an adequate absorbent of ethylene oxide for use instead of conventional water, but the following are the properties required for an absorbent for ethylene oxide:

1) excellent absorbing power per weight, preferably the same as or greater than water;
2) low specific heat;
3) lack of reactivity with ethylene oxide and by-products;
4) does not solidify or deteriorate within the normal operating conditions of a plant; and
5) high boiling point, and small stripping and splashing loss.

SUMMARY OF THE INVENTION

The object of the present invention is to provide an absorbent which satisfies the requirements mentioned above and a recovery method using that absorbent.

Through earnest investigations under these circumstances, the inventors of the present invention have found that propylene carbonate fulfilled every requirement mentioned above for use as an absorbent for ethylene oxide, and completed the present invention by setting up processes employing propylene carbonate.

The present invention relates to a method of recovering ethylene oxide comprising the steps of:

bringing a mixed gas containing ethylene oxide into contact with an absorbent so as to cause the absorbent to absorb the ethylene oxide; and stripping and separating said ethylene oxide to recover it from said absorbent;

characterized in that the absorbent contains propylene carbonate.

That is:

1) the absorbing power per weight of propylene carbonate with respect to ethylene oxide is about 50% higher than that of water and about 40% higher than that of ethylene carbonate;

2) the specific heat of propylene carbonate is low at 0.4 cal/g.°C., which is similar to ethylene carbonate;

3) propylene carbonate is stable and has no direct reactivity with ethylene oxide, and further propylene carbonate is extremely stable against by-products such as aldehydes and acids which are produced in the ethylene oxidation step even more so than ethylene carbonate; and, 4) since the solidifying point of propylene carbonate is −49° C., there is no solidifying problem regarding actual operating conditions, and moreover, absorption of ethylene oxide can be carried out at 5 to 40° C., which does not require high equipment costs. For those excellent properties, there is no generation of impurities which consume ethylene oxide such as ethylene glycol, and further it becomes possible to set up an ethylene oxide absorption and stripping system which reduces the heat recovery loss resulting from cooling absorbent at the time of transfer from the stripping step to the absorption step to about one-third compared with a system employing water. These and other objects, features and advantages of the present invention will become clearer from the following description of the preferred embodiment taken in conjunction with the accompanying drawings.

DESCRIPTION OF THE PREFERRED EMBODIMENT (Propylene carbonate)

There are no restrictions regarding the propylene carbonate employed in the present invention, and those which are used industrially can be employed as is. Propylene carbonate may be applied alone or as a mixture with ethylene carbonate containing at least 40 wt. %, and preferably, 50 wt. % of propylene carbonate.

Hereinafter, propylene carbonate and a mixture with ethylene carbonate containing at least 40 wt. % of propylene carbonate will be inclusively referred to as propylene carbonate for convenience. As is mentioned below, though propylene carbonate used alone shows stronger absorbing power with respect to ethylene oxide, a mixture with ethylene carbonate may still be used as an absorbent for ethylene oxide without impairing the properties of propylene carbonate, if the mixture contains at least 40 wt. % of propylene carbonate. In this case, the decline of the absorbing power is about 10%, and problems such as blocking or solidifying on the surface of piping of heat exchangers for cooling do not occur (Mixed gas containing ethylene oxide)

According to the present invention, a mixed gas containing ethylene oxide means a mixture of ethylene oxide and other gases. A typical example is a reaction product gas containing ethylene oxide produced by the vapor phase catalytic oxidation of ethylene with oxygen over a silver catalyst. Generally, a reaction product gas contains 0.5 to 5% of ethylene oxide and also includes a trace of gases, such as unconverted oxygen, unconverted ethylene, generated water, carbon dioxide, nitrogen, methane and ethane, aldehydes such as formaldehyde and acetaldehyde, and organic acids such as acetic acid.

(Absorbing operation of ethylene oxide)

After cooling, the reaction product gas obtained from the ethylene oxidation step is introduced to an ethylene oxide absorption tower. The reaction product gas is supplied from the bottom of the tower, while the propylene carbonate used as an absorbent is supplied from the top of the tower, and a counter-flow contact between vapor and liquid phases is carried out. The temperatures of the gas and the absorbent supplied to the absorption tower are preferably in the ranges of about 20 to 80° C. and about 10 to 35° C., respectively. Most of ethylene oxide is absorbed in propylene carbonate by this operation. As propylene carbonate is a good absorbent for carbon dioxide, a portion of carbon dioxide is also absorbed. The results of the experiments indicate that most of the generated water was also absorbed in propylene carbonate. However, in regard to nitrogen, methane, ethylene, ethane and oxygen, only traces of these gases are absorbed in propylene carbonate which is similar to conventional systems using water. Those gases other than ethylene oxide are stripped together with ethylene oxide at the stripping tower, then the non-condensable gases are separated from ethylene oxide, and recycled to the entrance of the absorption tower.

As for to the operating conditions for the absorption tower, the molar flow rate ratio of the absorbent to the supplied ethylene oxide is usually 0.10 to 0.35 (L/V). The gas hourly space velocity (GHSV[NTP]) of a mixed gas containing ethylene oxide is usually 400 to 4000 $hr^{-1}$ under normal conditions. The operation of the absorption tower, i.e. the absorbing of ethylene oxide, usually proceeds within a temperature range of usually 5 to 50° C., and preferably 10 to 45° C. Though absorbing power becomes greater according to the deceasing of temperature, too low an operating temperature causes disadvantages, such as increasing the heat energy loss for cooling the absorbent to the low temperature or the necessity of a special coolant. On the other hand, too high an operating temperature requires a larger amount of absorbent, which means not only is greater energy required for circulating the absorbent, but an increased heat recovery loss. Further, if the absorption of ethylene oxide is not sufficient, unabsorbed ethylene oxide is recycled to the oxidation reactor, resulting in a product loss. Therefore, the above mentioned temperature range is appropriate. In addition, the absorbing power of propylene carbonate is greater than that of ethylene oxide, thus the operation can be proceeded economically at a temperature of above 40° C.

Operation pressure of the absorption tower is usually 2 to 40 $kg/cm^2$.G, and preferably 10 to 30 $kg/cm^2$.G. Though the absorbing operation becomes more efficient according to an increase in pressure, the possible range is almost completely determined by the operating pressure of the oxidation reactor. From the results of studies of absorption performed by the inventors of the present invention, absorbing power with respect to ethylene oxide expressed by per unit weight of an absorbent was about 150% that of water for propylene carbonate and about 110% of water for ethylene carbonate. Therefore, compared with conventional methods using water, it is possible to reduce the amount of the absorbent 40 to 50%, or increase the operating temperature of the absorption tower.

(Stripping and separation of ethylene oxide)

After heating, the propylene carbonate solution with ethylene oxide absorbed therein is supplied to the top of an ethylene oxide stripping tower, and the ethylene oxide is stripped therefrom by gas-liquid contact with a stripping gas supplied at the bottom of the tower. The operating conditions are a normal temperature range at the top of tower of 80 to 140° C., and preferably 85 to 120° C., at the top of the tower, and a normal pressure range of 0.1 to 3 $kg/cm^2$.G, and preferably 0.3 to 1.5 $kg/cm^2$.G. The temperature and pressure at the bottom of the tower become higher because of the pressure loss caused by trays or packing provided inside the tower placed for the gas-liquid contact. Generally, the temperature difference between the top and the bottom is 10 to 25° C.

In conventional systems using water, heated steam of the water itself is employed as a stripping gas, because even if other non-condensable gases such as nitrogen and carbon dioxide are used, it is difficult to avoid a large amount of accompanying water, since the boiling point of water under normal pressure: is low at 100° C. While the latent heat of vaporization for water is large at about 500 kcal/kg, while the temperature of the top of the tower is as low as 80 to 140° C., thus it is difficult to recover the heat carried away by the accompanying water vapor efficiently. For the stripping step of the present invention using propylene carbonate, stripping gases are not necessary, stripping by heat alone is sufficient. Stripping gases, however, may be employed depending on necessity. Examples of these gases are non-condensable gases such as carbon dioxide recovered by separation in a carbon dioxide removal step, ethylene, which is a raw material for catalytic oxidation, or methane, which is a diluent gas for catalytic oxidation. When using these gases, the amount of propylene carbonate, which is stripped together with ethylene oxide and other components, can be reduced to an amount so small as to be ignored, since the boiling point of propylene carbonate is high at 242° C. Only the amount of water corresponding to the amount which is produced by a side reaction in the oxidation reactor can be stripped at this stripping step. A portion of the aldehydes and organic acids is stripped together simultaneously.

In conventional absorption and stripping systems using water, the absorbent water, which absorbed ethylene oxide at the absorption tower, is exposed to a temperature (80 to 140° C.) which is high enough to produce ethylene glycol, at the time of supplying the absorbent to the stripping tower. Thus, it is inevitable that a large amount of ethylene glycol is produced as a by-product. 3% to 15% of the total ethylene oxide reacts in this step. Further it is very difficult and also requires a lot of energy to recover high grade ethylene glycol from this absorbent water containing aldehydes and organic acids which are by-products of the oxidation process. In the present invention, the absorbent contains almost no water, i.e., about 0 to 5 wt. %. Therefore, production of ethylene glycol can be decreased to become less than one-thousandth to one-hundredth of that of conventional systems using water. Although the lower the stripping pressure the better and the process can be carried out with a small amount of stripping gas, as described above the pressure should be maintained as high as needed to allow gases or liquid to flow down in the ethylene oxide purification step after the stripping.

After the ethylene oxide stripping, propylene carbonate is removed from the bottom of the stripping tower, then cooled and recycled to the ethylene oxide absorption tower. It is desirable that mutual heat exchange is performed between the absorbent at the bottom of the stripping tower (referred to as bottom absorbent, hereinafter) and the bottom absorbent of the absorption tower. At this time, it is also preferable to control the temperature of the bottom absorbent of the stripping tower in the range of about 10 to 35° C. by cooling, and the temperature of the bottom absorbent of the absorption tower in the range of about 70 to 150° C. by heating. Though a part of their retention heat is recovered by this heat exchange, if the temperature of the bottom absorbent of the absorption tower is below 70 to 100° C., actual heat recovery generally becomes difficult, due to too small a temperature difference between the low temperature medium and the high temperature medium. In this case, the retention heat is allowed to be heat exchanged with cooling water (sea water, recooled water, industrial water, etc., at 10 to 30° C.) whereby heat is not recovered, but is instead removed out of this system. In conventional systems using water, the specific heat of water is high at 1 kcal/kg° C., while in the present invention the specific heat of propylene carbonate is about 0.4 kcal/kg° C., which is only about 40% that of water. Thus, even if the same amount (weight) of absorbent as water is used, the heat recovery loss from the above mentioned cooling step can be reduced by as much as 60%. Moreover, the absorbing power with respect to ethylene oxide is 150% of water or propylene carbonate and 110% of water for ethylene carbonate, respectively. Therefore, it is possible to decrease the amount of absorbent or increase the operating temperature of the absorption tower, which can reduce the heat recovery loss to 25 to 30% of a system using water.

In the case of long-term operation, an extremely small amount of circulating absorbent must be removed from the system, since aldehydes, organic acids and trace amounts of ethylene glycol will accumulate little by little in the absorbent (propylene carbonate). However, this amount is approximately 0.002% of the total circulating absorbent per 1 hour, which may be ignored compared with the amount of ethylene oxide reactant produced by conventional methods using water. Further, the difference of the boiling points between those impurities and propylene carbonate is so large that the removed absorbent can be recovered as reusable propylene carbonate by conventional distillation techniques and the like.

In addition, those operations such as adding a stabilizer (neutralizer, etc.) for corrosion prevention, and removing those impurities from the absorbent by passing through an apparatus packed with an adsorbent, may be performed without impairing the effects of the present invention.

(Process flow)

Figure 1:
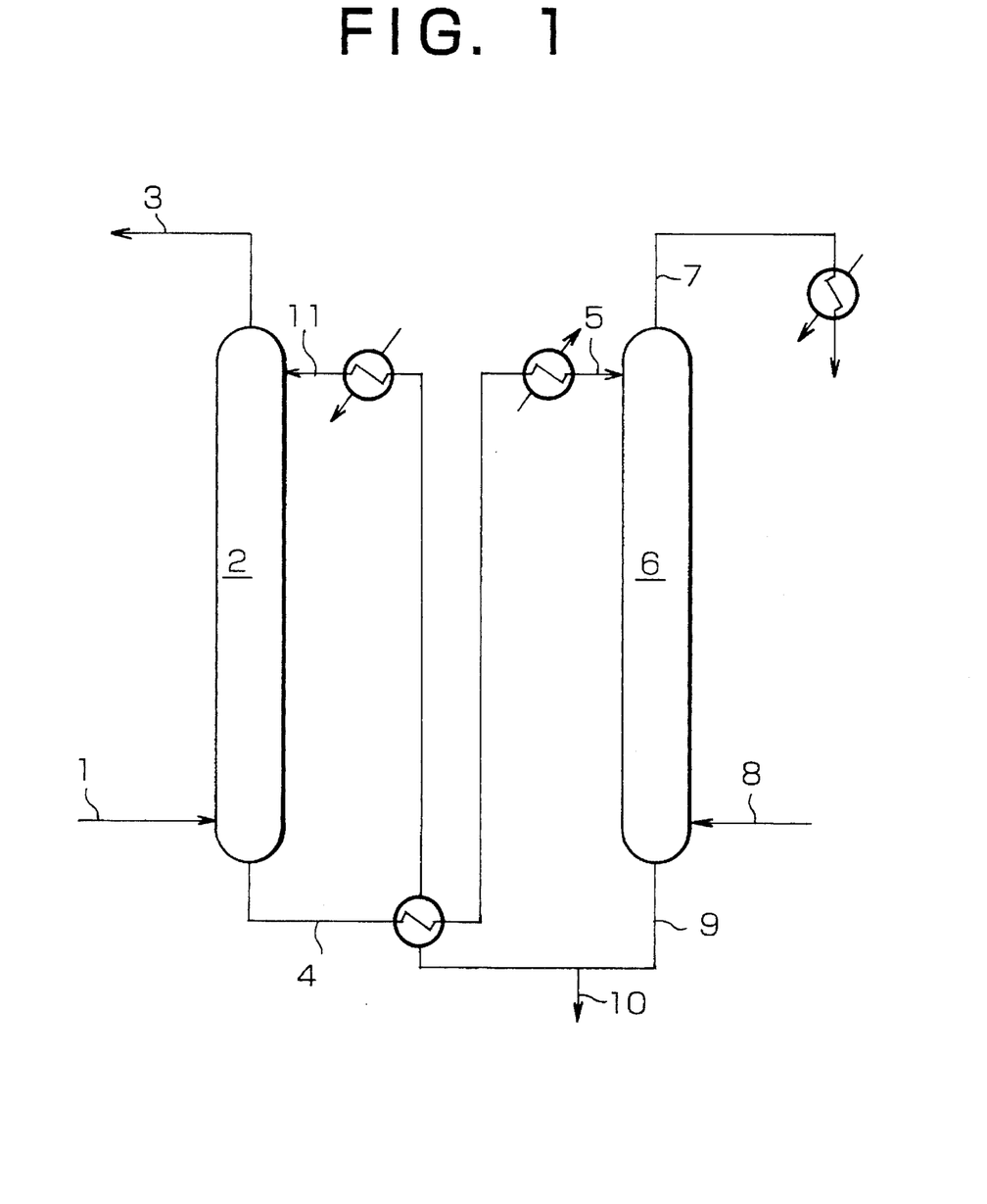
FIG. 1 shows a process assembling example according to the present invention.

A constructional example of a process according to the present invention is illustrated in FIG. 1. The construction of each operation device unit and the piping are almost the same as the existing system using water as an absorbent. A reaction product gas containing ethylene oxide, obtained by vapor phase catalytic oxidation of ethylene with oxygen over a silver catalyst, is supplied to the bottom of an ethylene oxide absorption tower (2) via a conduit (1). This reaction product gas is placed in counter-flow contact with an absorbent (propylene carbonate) supplied via a conduit (11) from the top of the tower, and more than 99 wt. % of the ethylene oxide is absorbed in the absorbent (propylene carbonate). At the same time, a portion of gases such as carbon dioxide, generated water and ethylene are absorbed therein. Unabsorbed gases (including ethylene, oxygen, carbon dioxide, nitrogen, argon, methane, ethane, and the like) are circulated via a conduit (3) to the carbon dioxide separation step and the oxidation step. The absorbent having absorbed ethylene oxide therein is heat exchanged with a bottom absorbent of an ethylene oxide stripping tower (6) via a conduit (4), further heated, for example, with team, to a temperature sufficient for stripping, and introduced to the ethylene oxide stripping tower (6). From the bottom of this stripping tower, the required stripping gas required for stripping is supplied via a conduit (8). A portion of a gas containing mainly carbon dioxide, ethylene, which is a raw material gas for the oxidation process, and methane, which is a diluent gas for the oxidation process, can be used as the stripping gas. Stripped gas comprising mainly ethylene oxide is sent to the ethylene oxide purification step via a conduit (7) to isolate water and gases having low boiling points after cooling (omitted from the figure). A portion of some of the gases having low boiling points separated at this purification step, is recycled to a conduit (8) as a stripping gas for ethylene oxide. After stripping, the absorbent (propylene carbonate) is removed from the bottom of the stripping tower via a conduit (9) (a very small amount is removed from this system via a conduit (10) at this step to avoid accumulation of aldehydes and acidic materials), heat exchanged with the bottom absorbent of the ethylene oxide absorption tower, then recycled to a conduit (11) as an absorbent for ethylene oxide after further cooling.

The present invention will be illustrated in more detail by reference to the following examples, although the invention is not restricted by these examples.

EXAMPLES 1 to 11 and Comparative Examples 1 to 9

Figure 4:
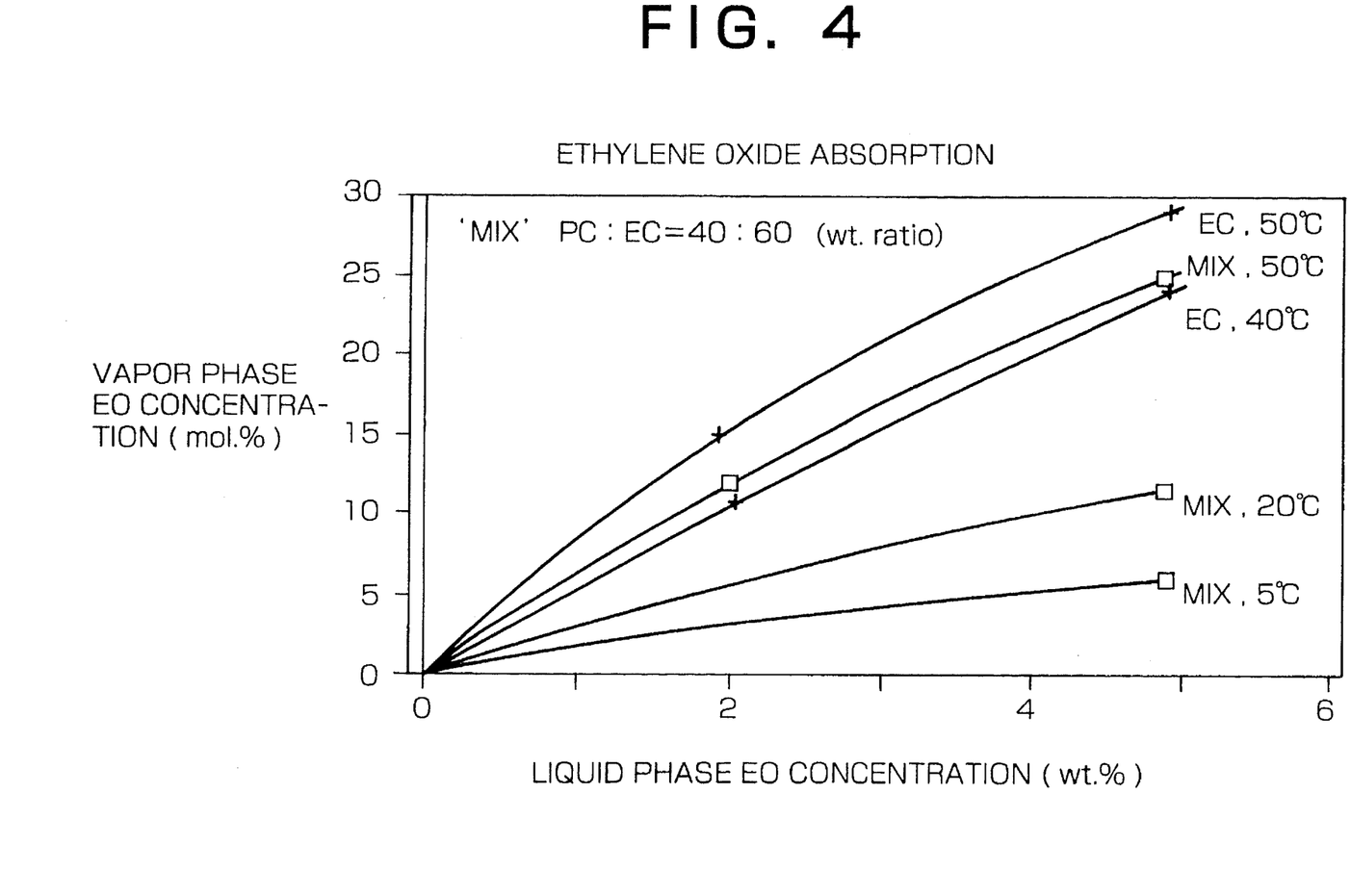
FIG. 4 shows the absorbing power of EC and a mixture of PC and EC with respect to ethylene oxide.

An autoclave whose volume was 1.5 L was used to determine the absorption equilibrium of ethylene oxide with respect to water, propylene carbonate, ethylene carbonate, and a mixture of propylene carbonate and ethylene carbonate. 500 cc of any one of the above mentioned liquids was transferred into the autoclave, wherein the inside was purged by nitrogen, and heated to the prescribed temperature. After the temperature reached a stable condition, the pressure was adjusted to 0.2 kg/cm$^2$.G. Thereafter, the prescribed amount of ethylene oxide was supplied thereto via a feed supplying pipe. To ensure that the supply of the ethylene oxide (EO) left in the pipe was supplied to the autoclave, 0.2 kg/cm$^2$. min of additional nitrogen was sent through the same pipe. This was followed by 4 hours of continuous stirring (600 rpm) and temperature control. The pressure was then recorded, and a sampling of the gas and the liquid was performed to determine the composition of the vapor phase and the liquid phase by gas chromatography. The ethylene oxide concentrations in the vapor phase which were calculated by partial pressure measurement values and the analysis of gas chromatography were compared, showing good such problems. For example, the absorbing power of PC at 20° C. is about 4 times larger than that of EC at 50° C. A comparison between EC and a mixture of PC and EC (PC:EC=40:60) is shown in FIG. 4. Similarly, it is shown that the absorbing power of the mixture is about 130% of EC at the same temperature.

TABLE 1

ETHYLENE OXIDE ABSORPTION

| Example No. | Absorbent | Temperature (°C.) | Total pressure (kg/cm²G) | N₂-partial pressure (kg/cm²G) | EO-partial pressure (kg/cm²G) | Ordinate axis Vapor phase EO concentration (mol %) | Abscissa axis Liquid phase EO concentration (wt %) |
|---|---|---|---|---|---|---|---|
| 1 | PC | 5 | 0.51 | 0.43 | 0.08 | 5.34 | 5.0 |
| 2 | PC | 20 | 0.46 | 0.40 | 0.06 | 4.08 | 2.0 |
| 3 | PC | 20 | 0.59 | 0.43 | 0.16 | 10.03 | 5.0 |
| 4 | PC | 40 | 0.54 | 0.42 | 0.12 | 7.76 | 2.0 |
| 5 | PC | 40 | 0.76 | 0.43 | 0.33 | 18.62 | 5.0 |
| 6 | PC | 50 | 0.60 | 0.42 | 0.18 | 10.82 | 2.0 |
| 7 | PC | 50 | 0.83 | 0.40 | 0.43 | 23.21 | 5.0 |
| 8 | PC:EC = 40:60 | 5 | 0.51 | 0.42 | 0.09 | 5.69 | 5.0 |
| 9 | PC:EC = 40:60 | 20 | 0.60 | 0.42 | 0.18 | 11.02 | 5.0 |
| 10 | PC:EC = 40:60 | 50 | 0.60 | 0.41 | 0.19 | 11.80 | 2.0 |
| 11 | PC:EC = 40:60 | 50 | 0.90 | 0.42 | 0.48 | 24.72 | 5.0 |

| Comparative Example No. | Absorbent | Temperature (°C.) | Total pressure (kg/cm²G) | N₂-partial pressure (kg/cm²G) | EO-partial pressure (kg/cm²G) | Ordinate axis Vapor phase EO concentration (mol %) | Abscissa axis Liquid phase EO concentration (wt %) |
|---|---|---|---|---|---|---|---|
| 1 | H₂O | 5 | 0.56 | 0.43 | 0.13 | 8.12 | 5.0 |
| 2 | H₂O | 20 | 0.51 | 0.41 | 0.10 | 6.31 | 2.0 |
| 3 | H₂O | 20 | 0.64 | 0.39 | 0.25 | 14.91 | 5.0 |
| 4 | H₂O | 40 | 0.56 | 0.37 | 0.19 | 11.82 | 2.0 |
| 5 | H₂O | 40 | 0.93 | 0.42 | 0.51 | 26.03 | 5.0 |
| 6 | EC | 40 | 0.59 | 0.42 | 0.17 | 10.59 | 2.1 |
| 7 | EC | 40 | 0.86 | 0.41 | 0.45 | 23.80 | 5.0 |
| 8 | EC | 50 | 0.68 | 0.43 | 0.25 | 14.81 | 2.0 |
| 9 | EC | 50 | 1.00 | 0.41 | 0.59 | 28.85 | 5.0 |

Note;
PC: Propylene carbonate
EC: Ethylene carbonate
EO: Ethylene oxide
Solidifying point of PC-EC mixed solution

| PC concentration (wt %) | 0 | 5 | 10 | 20 | 30 | 35 | 40 | 100 |
|---|---|---|---|---|---|---|---|---|
| Solidifying point (°C.) | 39 | 32 | 28 | 22 | 16 | 6 | <0 | −49 | correlation within ±3%. The results are shown in Table 1.

Figure 2:
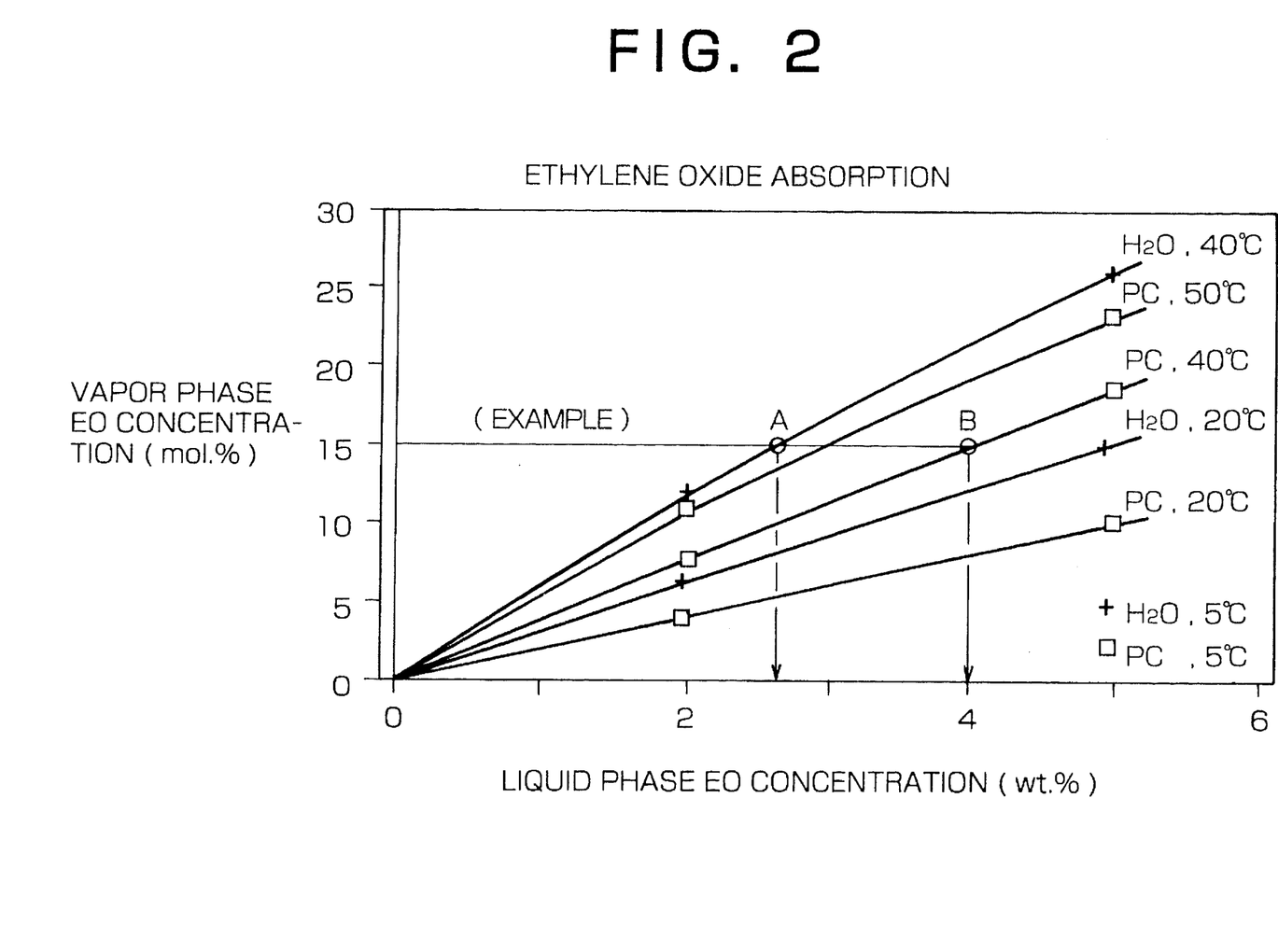
FIG. 2 shows the absorbing power of PC and water with respect to ethylene oxide. The example indicates that at 40° C., with the same vapor phase EO concentration (15 mol.%), the liquid phase EO concentrations are 2.6 wt. % for water (point A), 4.0 wt. % for PC (point B),respectively, and therefore the absorbing power of PC is about 150% of water (4.0/2.6≈1.5).
Figure 3:
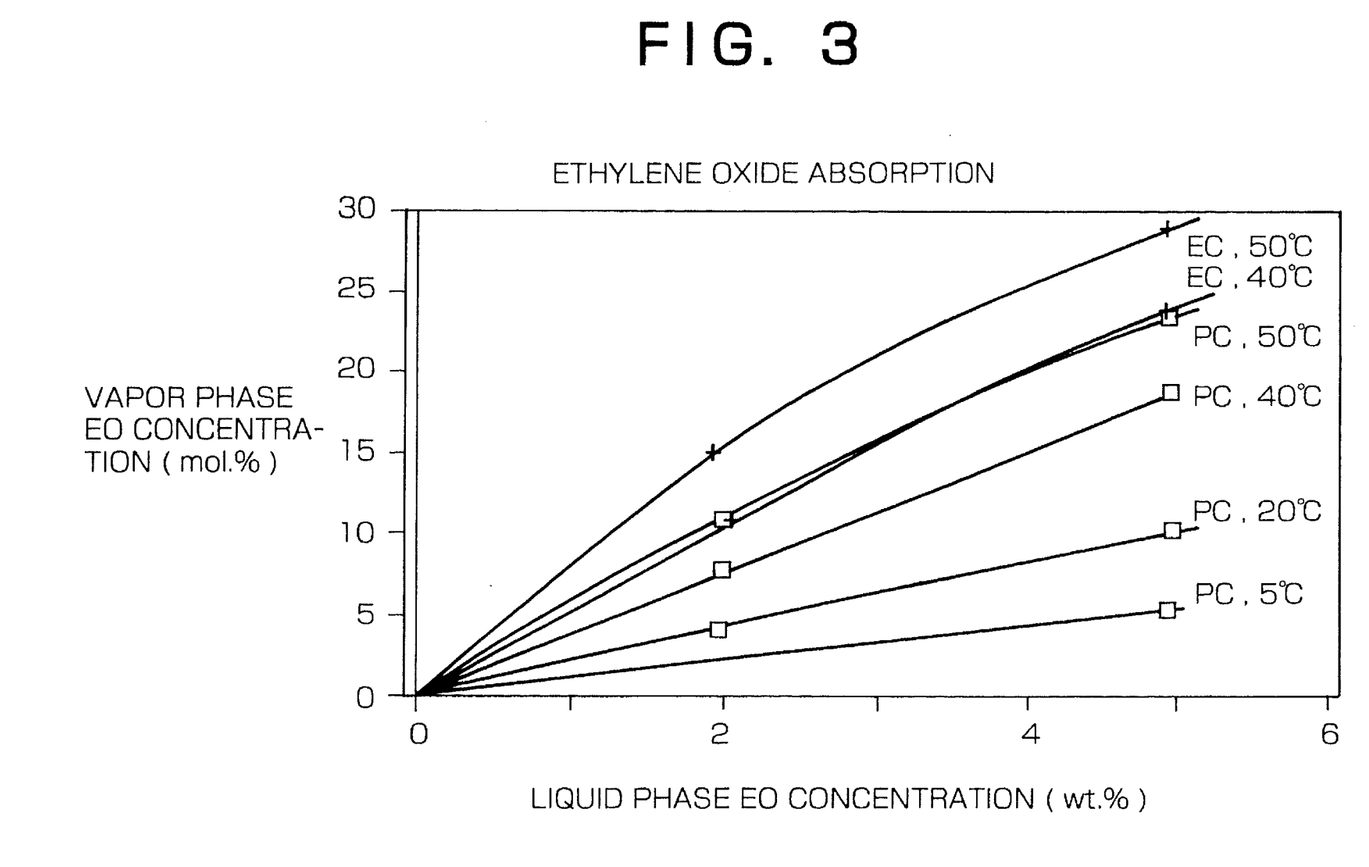
FIG. 3 shows the absorbing power of PC and EC with respect to ethylene oxide.

Examples 1 to 7 provide data concerning absorbing power with respect to ethylene carbonate (EC) which was obtained with propylene carbonate (PC), Examples 8 to 11 provide the same data obtained with a mixture of propylene carbonate and ethylene carbonate (MIX), Comparative Examples 1 to 5 provide the same data obtained with water, and Comparative Examples 6 to 9 provide the same data obtained with ethylene carbonate (EC). The data is illustrated in FIGS. 2 to 4. A comparison between PC and water is shown in FIG. 2. The liquid phase EO concentration, at the vapor phase EO concentration of 15 mol.% and at a temperature of 40° C., is 2.6 wt. % for water and 4.0 wt. % for PC, as shown-by example in FIG. 2. It can therefore be understood from FIG. 2 that the absorbing power of PC is approximately 150% of water. A comparison between PC and EC is shown in FIG. 3. Similarly, it is shown that the absorbing power of PC is about 140% of EC at the same temperature. Although, this comparison is made at the same temperature, it is actually difficult to operate plants with EC below approximately 50° C. because of problem with solidification, while to operate at this temperature with PC does not entail any

EXAMPLE 12

Employing propylene carbonate as an absorbent, the absorption tower was operated using an outflow gas (100 Nm³/hr). from the oxidation reactor of ethylene oxide. The above mentioned gas was supplied to the bottom of the absorption tower, wherein a Raschig ring like material was packed in order that the gas-liquid contact was sufficiently carried out. The outflow gas from the oxidation reactor contained not only ethylene oxide but also ethylene, oxygen, reaction by-products such as carbon dioxide, water, inert gases (nitrogen, methane, argon, ethane, etc.), and aldehydes. The absorption ratio of ethylene oxide and water corresponding to operating conditions of the absorption tower and other working conditions are shown in Table 2. Those components which are not shown in Table 2 were barely absorbed. [L/V] shown in Table 2 represents the ratio of the molar flow rate of the absorbent to the supplied EO gas.

EXAMPLE 13 to 15

Examples 13 and 14 provide results according to a change of the operating temperature of the absorption tower from 20° C. to 30° C. and 40° C. Although, the amount of the absorbent must be increased according to the increase of the absorbing temperature, the absorption of ethylene oxide thereby improved. The results obtained from a mixture of propylene carbonate and ethylene carbonate are described in Example 15.

EXAMPLE 16

In order to recover the ethylene oxide from the propylene carbonate which had absorbed ethylene oxide therein by the operation of Example 12, the absorbent was introduced to the ethylene oxide stripping tower. The propylene carbonate was depressurized and simultaneously stripped of ethylene oxide using carbon dioxide as the stripping gas. The operating conditions and results of the stripping are shown in Table 3. The bottom of the stripping tower was also packed with a Raschig ring like material to enable favorable contact between the carbon dioxide (for stripping) from the bottom and the propylene carbonate flowing down from the top. Since most of the water generated in the oxidation reactor could be stripped, accumulation of water in the propylene carbonate could be avoided. Also, the propylene carbonate did not react with the ethylene oxide, thus it was possible to avoid the production of ethylene oxide consuming materials such as ethylene glycol. As mentioned above, reaction products contained a small amount of aldehydes and acidic products (acetic acid etc.). A portion of these reaction products (particularly aldehydes) was stripped together with ethylene oxide, however, it was difficult to strip all of them. Therefore, a very small amount of absorbent was removed, followed by the adding of new absorbent. From several trials, it was found that 0.002% of the total absorbent per hour should be removed. This amount was so small as to be ignored when compared with the ethylene oxide loss resulting from the reaction of 3 to 15% of ethylene oxide produced in the oxidation reactor, by conventional methods using water as an absorbent. The above mentioned operation was maintained continuously for 35 days to check if there are any changes in absorption rate, stripping rate, quality of absorbent, and dissipation of absorbent. No such changes were observed and the operation was able to proceed stably. [L/V] shown in Table 3 represents the ratio of molar flow rate of the absorbent to supplied EO gas.

TABLE 2

| Example No. | Absorbent | Temperature (°C.) | Pressure (kg/cm²G) | Amount of raw gas (Nm³/hr) | Amount of absorbent (kg/hr) | L/V (mol) | Gas composition before absorption EO (mol %) | H₂O (mol %) | Absorbing ratio EO (%) | H₂O (%) |
|---|---|---|---|---|---|---|---|---|---|---|
| 12 | PC | 20 | 15 | 100 | 60 | 0.14 | 3.0 | 3.0 | 99.8 | 99> |
| 13 | PC | 30 | 15 | 100 | 88 | 0.20 | 3.0 | 3.0 | 99.7 | 99> |
| 14 | PC | 40 | 15 | 100 | 120 | 0.27 | 3.0 | 3.0 | 99.8 | 99> |
| 15 | PC:EC = 40:60 | 40 | 15 | 100 | 135 | 0.30 | 3.0 | 3.0 | 99.7 | 99> |

TABLE 3

| Example No. | Absorbent | Temperature (°C.) | Pressure (kg/cm²G) | Stripping gas | Amount of stripping gas (Nm³/hr) | L/V (mol) | Absorbent composition before stripping EO (wt %) | H₂O (wt %) | Stripping ratio EO (%) | H₂O (%) |
|---|---|---|---|---|---|---|---|---|---|---|
| 16 | PC | 95 | 1.0 | $CO_2$ | 0.91 | 21 | 8.6 | 2.9 | 98 | 82 |
| 17 | PC | 105 | 1.0 | $CO_2$ | 0.97 | 26 | 6.1 | 2.5 | 99 | 80 |
| 18 | PC | 120 | 1.0 | $CO_2$ | 0.96 | 34 | 4.6 | 1.9 | 98 | 83 |
| 19 | PC:EC = 40:60 | 105 | 1.0 | $C_2H_4$ | 1.48 | 24 | 4.1 | 1.7 | 97 | 80 |

EXAMPLE 17 to 19

In Examples 17 to 19, ethylene oxide was stripped at the same stripping tower as example 16 from the absorbent obtained in Examples 13 to 15. The results are shown in Table 3. The operating temperature of the stripping tower was changed to 105° C., 120° C. and 105° C. (mixture), respectively. In each example, it was possible to recover ethylene oxide and water efficiently.

COMPARATIVE EXAMPLE 10

An operation was performed under conditions similar to Example 12, except ethylene carbonate was employed as an absorbent whose temperature and pressure at the entrance of the absorption tower was 40° C. and 18 kg/cm².G, respectively. Since solidifying, which occurred inside the absorbent supplying conduit having a temperature regulating cooling jacket, impeded a continuous supply of absorbent, constant absorption of ethylene oxide was not possible.

From the above results, it is obvious that propylene carbonate or a mixture with ethylene carbonate containing at least 40 wt. % of propylene carbonate, which are employed in the present invention, have the following excellent properties as an absorbent for ethylene oxide compared with conventionally used water. 1) The absorbing power per unit weight of ethylene oxide is high, at about 140 to 150% that of water. 2) The specific heat is small, at about 40% that of water. This property together with the property mentioned above enables the heat recovery loss, which arose from the repeated heating and cooling between the absorption system and the stripping system, to decrease to 25 to 30% of the system using water. Ethylene carbonate alone cannot achieve such a decrease of loss because of solidifying problems. 3) Propylene carbonate is extremely stable with respect to ethylene oxide and by-products from the oxidation reactor, such as aldehydes and organic acids. Thus, almost all the absorbed ethylene oxide can be recovered as ethylene oxide with almost no by-products such as ethylene glycol. That means a flexible production system can be applied in accordance with recent economic conditions and production demands. 4) As the solidifying point of propylene carbonate is at least below the freezing point, solidifying and blocking do not occur on the contacting surface with the cooling heat exchanger. Even if the plant is not in operation, special curing is not necessary to avoid solidifying. 5) There is little splashing loss during the absorption and stripping steps, since the boiling point of propylene carbonate is at about 240° C. The above properties enable the constructing of an ethylene oxide plant which is economically superior and flexible. More specifically, according to this recovery method, the recovery loss of ethylene oxide in the absorption and stripping steps and energy consumption become smaller compared with conventional methods employing an absorbent having water as a main component.

What is claimed is:

1. A method of recovering ethylene oxide comprising the steps of:

bringing a mixed gas containing ethylene oxide into contact with an absorbent so as to cause said absorbent to absorb said ethylene oxide; and stripping and separating said ethylene oxide to recover it from said absorbent;

characterized in that said absorbent contains propylene carbonate.

2. A method according to claim 1, using a mixture, containing ethylene carbonate and at least 40 wt. % of propylene carbonate, as said absorbent.

3. A method according to claim 1, wherein said absorption of said mixed gas containing ethylene oxide is carried out by contacting said absorbent with said mixture at an absorption tower, followed by introducing the resulting absorbent (a) to a stripping tower, recovering said ethylene oxide by stripping from the top of said stripping tower, said method further comprising recycling the absorbent (b) which is stripped of the ethylene oxide to said absorption tower, while realizing heat exchange between said absorbent (a) and said absorbent (b) and further heating said absorbent (a) and cooling said absorbent (b), thereby controlling the temperatures of said absorbent (a) and said absorbent (b) within a range of 70 to 150° C. and 10 to 35° C., respectively.

4. A method according to claim 1 wherein 0.5 to 5 volume % of ethylene oxide is contained in said mixed gas.

5. A method according to claim 3 wherein the temperature of said mixed gas containing ethylene oxide supplied to said absorption tower is maintained at from 20 to 80° C.

6. A method according to claim 3 wherein the temperature of said absorbent supplied to said absorption tower is maintained at from 10 to 35° C.

7. A method according to claim 1 wherein said mixed gas mentioned above is a reaction product gas obtained from the vapor phase catalytic oxidation of ethylene with oxygen over a silver catalyst.

8. A method according to claim 1 wherein said absorption of said ethylene oxide is carried out within a temperature range of 5 to 50° C.

9. A method according to claim 1 wherein said absorption of said ethylene oxide is carried out within a pressure range of 2 to 40 kg/cm$^2$.G.

10. A method according to claim 1 wherein said stripping of said ethylene oxide is carried out at said stripping tower while the temperature at the top of said stripping tower is maintained at from 80 to 140° C.

11. A method according to claim 1 wherein said stripping of said ethylene oxide is carried out within a pressure range of 0.1 to 3 kg/cm$^2$.G.

12. A method according to claim 1 wherein said stripping of said ethylene oxide is carried out by heating.

13. A method according to claim 1 wherein said stripping of said ethylene oxide is carried out using a stripping gas comprising steam, carbon dioxide, which is a by-product of catalytic oxidation, ethylene, which is a raw material for catalytic oxidation, or methane, which is a diluent gas or catalytic oxidation.

* * * * *